United States Patent
St. Laurent et al.

(10) Patent No.: US 9,643,912 B2
(45) Date of Patent: *May 9, 2017

(54) FATTY ALCOHOL ESTERS OF HYDROXYCARBOXYLIC ACIDS

(71) Applicant: CHEMSMART, LLC, Canton, MA (US)

(72) Inventors: Joseph P. St. Laurent, Lakeville, MA (US); Scott A. Goodrich, Stoughton, MA (US); Gerald S. Jones, Jr., Norwood, MA (US)

(73) Assignee: CHEMSMART, LLC, Canton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/939,422

(22) Filed: Nov. 12, 2015

(65) Prior Publication Data

US 2016/0060206 A1    Mar. 3, 2016

Related U.S. Application Data

(63) Continuation of application No. 13/823,406, filed as application No. PCT/US2011/051960 on Sep. 16, 2011, now Pat. No. 9,315,446.

(60) Provisional application No. 61/383,894, filed on Sep. 17, 2010.

(51) Int. Cl.
    *C07C 69/68*      (2006.01)
    *C12P 7/62*      (2006.01)
    *C08G 65/332*      (2006.01)

(52) U.S. Cl.
     CPC .......... *C07C 69/68* (2013.01); *C08G 65/3322* (2013.01); *C12P 7/62* (2013.01); *C12Y 301/01003* (2013.01); *C07B 2200/07* (2013.01); *Y02P 20/52* (2015.11)

(58) Field of Classification Search
     CPC ....... C07C 69/68; C08G 65/3322; C12P 7/62; C12Y 301/01003; C07B 2200/07; Y02P 20/52
See application file for complete search history.

(56) References Cited

U.S. PATENT DOCUMENTS

| | | | |
|---|---|---|---|
| 4,115,415 A | 9/1978 | Yoshihara et al. | |
| 7,186,272 B2 | 3/2007 | Heller | |
| 7,544,366 B1 | 6/2009 | Lutz et al. | |
| 9,315,446 B2 * | 4/2016 | St. Laurent | C07C 69/68 |
| | | | 560/189 |

FOREIGN PATENT DOCUMENTS

JP      H06-179814 A      6/1994

OTHER PUBLICATIONS

Cammack, R Attwood et al., Oxford Dictionary of Biochemistry and Molecular Biology, 2nd Edition, Oxford University Press, 2006.
Davies et al., "Importance of Chirality in Drug Therapy and Pharmacy Practice: Implications for Psychiatry", Advances in Pharmacy, 1(3), pp. 242-252, (2003).
International Preliminary Report on Patentability for PCT/US11/51960, mailed Mar. 19, 2013.
International Search Report and Written Opinion for PCT/US11/51960 dated Feb. 1, 2012.
Konigsberger, et. al., "The Synthesis of (R)- and (S)- a trifluoromethyl a hydroxycarboxylic acids via enzymatic resolutions" Terahedron: Asymmety 10 p. 679-687, Abstract p. 683, Fig 1 (1999).
Lunt, "Large Scale Production, Properties, and Commerical Applications of Polyactic Acid Polymers", Polymer Degradation and Stability, 59, 145-152, 1998.
Osanai et al., "Preparation and Antimicrobial Properties of Polyoxyethylene MonoAlkyl Ether Glycinates and Alaninates—Effects of Oxyethylene Group on the Antimicrobial Properties", J. Antifung. Agents, 15(4), pp. 157-162, (1987).
Patani et al., "Biososterism: A Rational Approach in Drug Design", Chem. Rev. 96, pp. 3147-3176, (1996).
Proposed Final Rulemaking for Skin Protectant Drug Products for Over the-counter Human Use; Fever Blister and Cold Sore Treatment Drug Products published by the United States Food and Drug Administration in the Federal Register, vol. 55, No. 21, Jan. 31, 1990, pp. 3362 to 3370.
Translation of Osanai et al., "Preparation and Antimicrobial Properties of Polyoxyethylene MonoAlkyl Ether Glycinates and Alaninates—Effects of Oxyethylene Group on the Antimicrobial Properties", J. Antifung. Agents, 15(4), pp. 157-162, (1987).

* cited by examiner

*Primary Examiner* — Paul A. Zucker
*Assistant Examiner* — Mark Luderer
(74) *Attorney, Agent, or Firm* — Lando & Anastasi, LLP

(57) ABSTRACT

Described herein are compositions (e.g., a pharmaceutical composition) and compounds of formula I, methods of making compounds of formula (I) and their use in the treatment and/or prevention of diseases and disorders.

23 Claims, No Drawings

FATTY ALCOHOL ESTERS OF HYDROXYCARBOXYLIC ACIDS

CLAIM OF PRIORITY

This application is a continuation of U.S. Ser. No. 13/823,406, filed Sep. 16, 2011, which is a national stage application under 35 U.S.C. §371 of International Application No. PCT/US2011/051960, filed Sep. 16, 2011, which claims priority to U.S. Ser. No. 61/383,894, filed Sep. 17, 2010, the content of each of which is incorporated by reference in its entirety.

TECHNICAL FIELD OF THE INVENTION

The invention relates to fatty alcohol esters of hydroxycarboxylic acids, their compositions and methods of use as a sclerosant (e.g., for treating varicose veins). The invention also relates to methods of making compounds of formula (I) in scalable (e.g., multi-kilogram scale) batches.

BACKGROUND OF THE INVENTION

Sclerotherapy is a treatment that intentionally damages the lining (endothelium) of small veins and is commonly used to treat blood vessel malformations such as varicose veins and spider veins. By doing this and then applying pressure the vein walls stick together. The vein can then no longer fill with blood and so it is obliterated. One commonly used Sclerosant is a fatty alcohol known as polidocanol. Polidocanol is the active ingredient used in the FDA-approved Asclera®.

To date, sclerotherapy is accomplished by injecting the the malformed veins with a sclerosing solution causing the target vein to shrink, and subsequently dissolve over a period of time as the body naturally absorbs the treated vein. While sclerotherapy is effective, there remains a need for a less invasive, more versatile sclerosant, i.e., one which may be administered in a number of different ways.

SUMMARY OF INVENTION

In one aspect, the present invention is directed to a compound of formula (I):

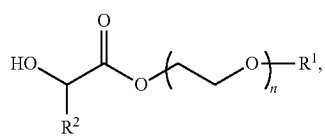

(I)

wherein
$R^1$ is a $C_{8-35}$ alkyl;
n is an integer from 2 to 35; and
$R^2$ is hydrogen, alkyl, aryl, heteroaryl, heterocyclyl or aralkyl;
or a pharmaceutically acceptable salt thereof.

In certain embodiments, n is an integer from 2 to 25. In some embodiments, n is an integer from 2 to 15. In some embodiments, n is an integer from 2 to 10. In some embodiments, n is an integer from 4 to 10. In some embodiments, n is 2. In some embodiments, n is 6. In some embodiments, n is 7. In some embodiments, n is 8. In some embodiments, n is 9. In some embodiments, n is 10. In some embodiments, n is 11. In some embodiments, n is 12.

In certain embodiments, $R^1$ is a $C_{8-25}$ alkyl group. In some embodiments, $R^1$ is a $C_{8-20}$ alkyl group. In some embodiments, $R^1$ is a $C_{10-15}$ alkyl group. In some embodiments, $R^1$ is a $C_{12}$ alkyl group.

In certain embodiments, $R^2$ is alkyl (e.g., $C_{1-4}$ alkyl). In certain embodiments, $R^2$ is $C_{1-4}$ alkyl (e.g., methyl). In certain embodiments, $R^2$ is aryl (e.g., phenyl). In some embodiments, $R^2$ is aralkyl (e.g., benzyl).

In certain embodiments, a compound described herein (e.g., a compound of formula (I)) is a racemic mixture (e.g., less than 10% enantiomeric excess of either the R or S stereoisomer). In certain embodiments, a compound described herein (e.g., a compound of formula (I)) is at least 10% enantiomeric excess of the R stereoisomer.

In certain embodiments, the compounds described herein (e.g., a compound of formula (I)) is at least 50% enantiomeric excess of the R stereoisomer. In some embodiments, the compound described herein (e.g., a compound of formula (I)) is at least 75% enantiomeric excess of the R stereoisomer. In some embodiments, the compound described herein (e.g., a compound of formula (I)) is at least 85% enantiomeric excess of the R stereoisomer. In some embodiments, the compound described herein (e.g., a compound of formula (I)) is at least 90% enantiomeric excess of the R stereoisomer. In some embodiments, the compound described herein (e.g., a compound of formula (I)) is at least 95% enantiomeric excess of the R stereoisomer. In some embodiments, the compound described herein (e.g., a compound of formula (I)) is least 97% enantiomeric excess of the R stereoisomer. In some embodiments, the compound described herein (e.g., a compound of formula (I)) is at least 99% enantiomeric excess of the R stereoisomer.

In certain embodiments, the compound described herein (e.g., a compound of formula (I)) is at least 10% enantiomeric excess of the S stereoisomer. In certain embodiments, the compound described herein (e.g., a compound of formula (I)) is at least 50% enantiomeric excess of the S stereoisomer. In some embodiments, the compound described herein (e.g., a compound of formula (I)) is at least 75% enantiomeric excess of the S stereoisomer. In some embodiments, the compound described herein (e.g., a compound of formula (I)) is at least 85% enantiomeric excess of the S stereoisomer. In some embodiments, the compound described herein (e.g., a compound of formula (I)) is at least 90% enantiomeric excess of the S stereoisomer. In some embodiments, the compound described herein (e.g., a compound of formula (I)) is at least 95% enantiomeric excess of the S stereoisomer. In some embodiments, the compound described herein (e.g., a compound of formula (I)) is at least 97% enantiomeric excess of the S stereoisomer. In some embodiments, the compound described herein (e.g., a compound of formula (I)) is at least 99% enantiomeric excess of the S stereoisomer.

In certain embodiments, the compound of formula (I) is represented by the following formula:

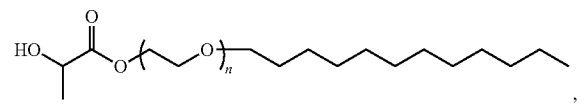

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9. In some embodiments, n is 10. In some embodiments, n is 11. In some embodiments, n is 12.

In some embodiments, the compound of formula (I) is represented by the following formula:

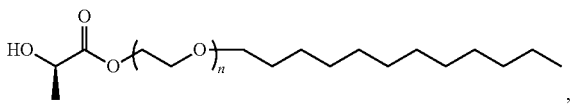

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some aspects of this embodiment, n is an integer from 4 to 10. In some embodiments, n is 6. In some embodiments, n is 7. In some embodiments, n is 8. In some embodiments, n is 9. In some embodiments, n is 10. In some embodiments, n is 11. In some embodiments, n is 12.

In some embodiments, the compound of formula (I) is represented by the following formula:

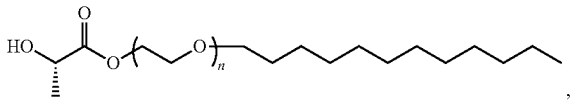

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9. In some embodiments, n is 10. In some embodiments, n is 11. In some embodiments, n is 12.

In certain embodiments, the compound of formula (I) may have an average molecular weight ranging from about 300 daltons to about 2000 daltons (e.g., from about 300 daltons to about 1500 daltons, from about 400 daltons to about 1200 daltons, from about 500 daltons to about 1000 daltons, from about 600 daltons to about 850 daltons).

The polymeric portion of a compound of formula (I) described herein may have a polymer polydispersity index (PDI) of less than or equal to about 2.5 (e.g., less than or equal to about 2.2, less than or equal to about 2.0, or less than or equal to about 1.5). In some embodiments, a hydrophobic polymer described herein may have a polymer PDI of about 1.0 to about 2.5, about 1.0 to about 2.0, about 1.0 to about 1.7, or from about 1.0 to about 1.6.

In another aspect, the invention is directed to a composition (e.g., a pharmaceutical composition) comprising a compound of formula (I).

In certain embodiments, the composition is substantially free of fatty alcohols (e.g., polidocanol). In some embodiments, the composition is substantially free of lactic acid or esters thereof (e.g., lactic acid methyl ester or lactic acid ethyl ester). In some embodiments, the composition is substantially free of a second sclerosant (e.g., a second compound for the treatment of varicose veins).

In some embodiments, the composition comprises an additional therapeutic agent. In certain embodiments, an additional therapeutic agent comprises an analgesic (e.g., fentanyl, morphine or codeine). In some embodiments, an additional therapeutic agent comprises an anti-inflammatory (e.g., ibuprofen or naproxen). In some embodiments, an additional therapeutic agent comprises an anesthetic (e.g., benzocaine or lidocaine). In some embodiments, an additional therapeutic agent comprises an opiod.

In certain embodiments, at least 50% by weight of the composition is a compound of formula (I). In some embodiments, at least 75% by weight of the composition is a compound of formula (I). In some embodiments, at least 85% by weight of the composition is a compound of formula (I). In some embodiments, at least 90% by weight of the composition is a compound of formula (I). In some embodiments, at least 95% by weight of the composition is a compound of formula (I). In some embodiments, at least 97% by weight of the composition is a compound of formula (I). In some embodiments, the composition consists essentially of a compound of formula (I).

In certain embodiments, the composition comprises a racemic mixture of the compound of formula (I) (e.g., less than 10% enantiomeric excess of either the R or S stereoisomer). In certain embodiments, the composition comprises at least 10% enantiomeric excess of an R stereoisomer of a compound of formula (I). In certain embodiments, the composition comprises at least 50% enantiomeric excess of an R stereoisomer of a compound of formula (I). In some embodiments, the composition comprises at least 75% enantiomeric excess of an R stereoisomer of a compound of formula (I). In some embodiments, the composition comprises at least 85% enantiomeric excess of an R stereoisomer of a compound of formula (I). In some embodiments, the composition comprises at least 90% enantiomeric excess of an R stereoisomer of a compound of formula (I). In some embodiments, the composition comprises at least 95% enantiomeric excess of an R stereoisomer of a compound of formula (I). In some embodiments, the composition comprises at least 97% enantiomeric excess of an R stereoisomer of a compound of formula (I). In some embodiments, the composition comprises at least 99% enantiomeric excess of an R stereoisomer of a compound of formula (I).

In certain embodiments, the composition comprises at least 10% enantiomeric excess of an S stereoisomer of a compound of formula (I). In certain embodiments, the composition comprises at least 50% enantiomeric excess of an S stereoisomer of a compound of formula (I). In some embodiments, the composition comprises at least 75% enantiomeric excess of an S stereoisomer of a compound of formula (I). In some embodiments, the composition comprises at least 85% enantiomeric excess of an S stereoisomer of a compound of formula (I). In some embodiments, the composition comprises at least 90% enantiomeric excess of an S stereoisomer of a compound of formula (I). In some embodiments, the composition comprises at least 95% enantiomeric excess of an S stereoisomer of a compound of formula (I). In some embodiments, the composition comprises at least 97% enantiomeric excess of an S stereoisomer of a compound of formula (I). In some embodiments, the composition comprises at least 99% enantiomeric excess of an S stereoisomer of a compound of formula (I).

In certain embodiments, the compound of formula (I) is represented by the following formula:

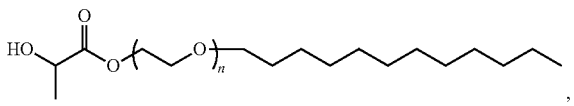

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In some embodiments, the compound of formula (I) is represented by the following formula:

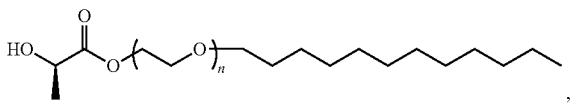

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In some embodiments, the compound of formula (I) is represented by the following formula:

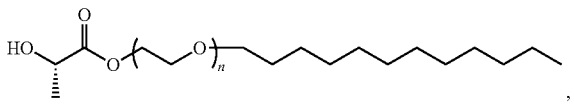

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In certain embodiments, the composition is in the form of an oil-in-water emulsion. In some embodiments, the composition is in the form of a water-in-oil emulsion. In some embodiments, the composition is in the form of a thickened aqueous gel. In some embodiments, the composition is in the form of a hydrophilic gel. In some embodiments, the composition is in the form of a capsule. In some embodiments, the composition is in the form of a tablet. In some embodiments, the composition is in the form of a hydrophobic ointment. In some embodiments, the composition is in the form of a hydrophilic ointment. In some embodiment, the composition is in the form of an anhydrous gel. In some embodiments, the composition is in the form of a solution. In some embodiments, the composition is in the form of an injectable foam.

In certain embodiments, the composition is configured for topical administration. In some embodiments, the composition is configured for oral administration. In some embodiments, the composition is configured for administration in the form of a gel, ointment, cream or patch (e.g., the composition is applied to a mounting that can be adhered to the skin of a subject). In some embodiments, the composition is configured for parenteral administration (e.g., the composition is prepared as a sterile solution using isotonic saline, Ringer's solution, water for injection (WFI) and sterile water for injection (SWFI)).

In another aspect, the present invention is directed to a method of treating varicose veins, the method comprising administering a compound of formula (I) or composition described herein.

In certain embodiments, the compound is administered topically. In some embodiments, the compound is administered via a gel, ointment, cream or patch. In certain embodiments, the composition is administered topically. In some embodiments, the composition is administered via a gel, ointment, cream or patch.

In certain embodiments, the method comprises administering a compound of formula (I) or composition as described herein once daily. In some embodiments, the method comprises administering a compound of formula (I) or composition as described herein twice daily. In some embodiments, the method comprises administering a compound of formula (I) or composition as described herein three times daily. In some embodiments, the method comprises administering a compound of formula (I) or composition as described herein four times daily. In some embodiments, the method comprises administering a compound of formula (I) or composition as described herein five times daily. In certain embodiments, the method comprises administering a compound of formula (I) or composition as described herein once weekly. In some embodiments, the method comprises administering a compound of formula (I) or composition as described herein once monthly.

In certain embodiments, the method includes a compound of formula (I) represented by the following formula:

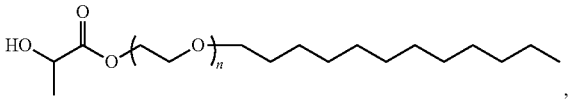

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In some embodiments, the method includes a compound of formula (I) represented by the following formula:

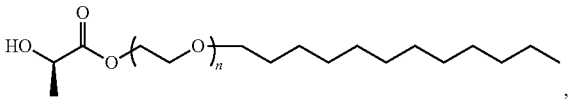

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In some embodiments, the method includes a compound of formula (I) represented by the following formula:

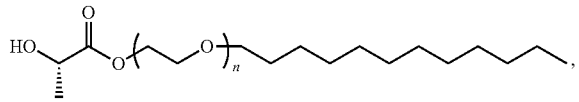

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In certain embodiments, the method includes a composition including a compound of formula (I) represented by the following formula:

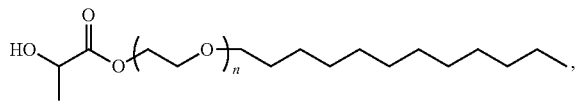

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In certain embodiments, the method includes a composition including a compound of formula (I) represented by the following formula:

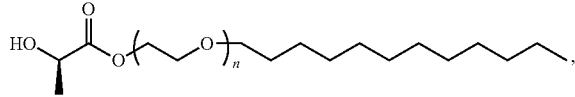

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In certain embodiments, the method includes a composition including a compound of formula (I) represented by the following formula:

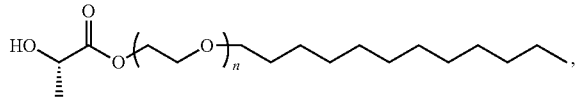

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In certain embodiments, the composition is administered topically. In some embodiments, the composition is administered via a patch. In some embodiments, the composition is administered orally. In some embodiments, the composition is administered parenterally (e.g., subcutaneous, intramuscular or intravenous injection).

In another aspect, the present invention is directed to a method of making a compound of formula (I), the method comprising reacting a fatty alcohol of formula (II):

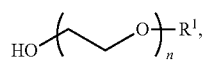

(II)

wherein
n is an integer from 2 to 35; and
$R^1$ is a $C_{8-35}$ alkyl;
with an α-hydroxy ester in the presence of enzymatic conditions in greater than 60% purity.

In certain embodiments, n is an integer from 2 to 25. In some aspects of this embodiment, n is an integer from 2 to 15. In some aspects of this embodiment, n is an integer from 2 to 10. In some embodiments, n is an integer from 4 to 10.

In certain embodiments, $R^1$ is a $C_{8-25}$ alkyl group. In some embodiments, $R^1$ is a $C_{10-20}$ alkyl group. In some embodiments, $R^1$ is a $C_{10-15}$ alkyl group. In some embodiments, $R^1$ is a $C_{12}$ alkyl group.

In certain embodiments, the method of making a compound of formula (I) is carried out in an open reaction vessel.

In certain embodiments, the method includes removing one of the products of the method. In some embodiments, the product is an alcohol. In certain embodiments, the product is an alcohol by-product. In some embodiments, the product is removed by using at least one of the following: evaporation under ambient conditions, evaporation facilitated by heat, rotary evaporation, convection, inert gas flow, application of vacuum, vacuum filtration, distillation, azeotropic distillation, vacuum distillation, chemical modification, enzymatic modification and adsorption.

In certain embodiments, the reaction is carried out on at least 50 g of the saturated alcohol starting material. In some embodiments, the reaction is carried out on at least 100 g of the saturated alcohol starting material. In some embodiments, the reaction is carried out on at least 200 g of the saturated alcohol starting material. In some embodiments, the reaction is carried out on at least 250 g of the saturated alcohol starting material. In some embodiments, the reaction is carried out on at least 400 g of the saturated alcohol starting material. In some embodiments, the reaction is carried out on at least 500 g of the saturated alcohol starting material.

In certain embodiments, the method comprises a batch process of producing a compound of formula (I).

In certain embodiments, the desired compound is produced in greater than 60% purity in the absence of a purification step. In some embodiments, the desired compound is produced in greater than 70% purity. In some embodiments, the desired compound is produced in greater than 70% purity in the absence of a purification step. In some embodiments, the desired compound is produced in greater than 80% purity. In some embodiments, the desired compound is produced in greater than 80% purity in the absence of a purification step. In some embodiments, the desired compound is produced in greater than 90% purity. In some embodiments, the desired compound is produced in greater than 90% purity in the absence of a purification step. In some embodiments, the desired compound is produced in greater than 95% purity. In some embodiments, the desired compound is produced in greater than 95% purity in the absence of a purification step. In some embodiments, the desired compound is produced in the absence of a purification step.

In certain embodiments, the saturated alcohol is polidocanol (also known as polydocanol). In some embodiments, the α-hydroxy ester is ethyl lactate. In some embodiments, the ethyl lactate is substantially the R stereoisomer. In some embodiments, the ethyl lactate is substantially the S stereoisomer. In some embodiments, the enzyme is a lipase enzyme. In some embodiments, the lipase enzyme is Novozym 435®.

In another aspect, the present invention is directed to a method of making a compound of formula (I), the method comprising reacting a fatty alcohol of formula (II):

wherein
n is an integer from 2 to 35; and
$R^1$ is a $C_{8-35}$ alkyl;
with an α-hydroxy ester in the presence of enzymatic conditions in greater than 60% yield.

In certain embodiments, the desired compound is produced in greater than 70% yield. In some embodiments, the desired compound is produced in greater than 80% yield. In some embodiments, the desired compound is produced in greater than 90% yield. In some embodiments, the desired compound is produced in greater than 95% yield.

wherein n is an integer from 2 to 35. In some aspects of this embodiment, n is an integer from 2 to 25. In some aspects of this embodiment, n is an integer from 2 to 15. In some aspects of this embodiment, n is an integer from 2 to 10. In some embodiments, n is an integer from 4 to 10. In some embodiments, n is 6. In some embodiments, n is 7. In some embodiments, n is 8. In some embodiments, n is 9.

In certain embodiments, $R^1$ is a $C_{8-25}$ alkyl group. In some embodiments, $R^1$ is a $C_{10-20}$ alkyl group. In some embodiments, $R^1$ is a $C_{10-15}$ alkyl group. In some embodiments, $R^1$ is a $C_{12}$ alkyl group.

In some embodiments, the α-hydroxy ester is ethyl lactate. In some embodiments, the ethyl lactate is substantially the R stereoisomer. In some embodiments, the ethyl lactate is substantially the S stereoisomer.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 carbon atoms in it. The term "haloalkyl" refers to an alkyl in which one or more hydrogen atoms are replaced by halo, and includes alkyl moieties in which all hydrogens have been replaced by halo, e.g., perfluoroalkyl. The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "aryl" refers to an aromatic monocyclic, bicyclic, or tricyclic hydrocarbon ring system, wherein any ring atom capable of substitution can be substituted, e.g., by one or more substituents. Examples of aryl moieties include, but are not limited to, phenyl, naphthyl, and anthracenyl.

The term "arylalkyl" or the term "aralkyl" refers to alkyl substituted with an aryl. Exemplary aralkyls include but are not limited to benzyl and phenethyl.

The term "cycloalkyl" as employed herein includes saturated cyclic, bicyclic, tricyclic or polycyclic hydrocarbon groups having 3 to 12 carbons. Any ring atom can be substituted, e.g., by one or more substituents. The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "emollient" is a hydrophobic material that provides softness, lubricity and smoothness to the skin and often forms a thin occlusive film which increases hydration by reducing transepidermal water loss (TEWL).

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%. Some of the compositions described herein contain an enantiomeric excess of at least 50%, 75%, 90%, 95%, or 99% (the S-enantiomer). In other words the compositions contain an enantiomeric excess of the S enantiomer over the R enantiomer.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, Si, P or S, e.g., carbon atoms and 1-3, 1-6, or 1-9 heteroatoms of N, O, Si, P or S if monocyclic, bicyclic, or tricyclic, respectively. The heteroatom may optionally be the point of attachment of the heterocyclyl substituent. Any ring atom can be substituted, e.g., by one or more substituents. The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, Si, P or S, e.g., carbon atoms and 1-3, 1-6, or 1-9 heteroatoms of N, O, Si, P or S if monocyclic, bicyclic, or tricyclic, respectively. Any ring atom can be substituted, e.g., by one or more substituents.

The term "humectant" is a polar hygroscopic material that increases hydration by drawing water from the environment to help retain water in the skin's upper layers.

The term "moisturizer" refers to a material that will increase the level of hydration of skin, mucous membrane, wound, lesion or scab.

As used herein, "polymer polydispersity index (PDI)" or "polymer polydispersity" refers to the distribution of molecular mass in a given polymer sample. The polymer PDI calculated is the weight average molecular weight divided by the number average molecular weight. It indicates the distribution of individual molecular masses in a batch of polymers. The polymer PDI has a value typically greater than 1, but as the polymer chains approach uniform chain length, the PDI approaches unity (1).

The term "sclerosant" refers to an injectable irritant that is used in the treatment of varicose veins and that causes inflammation and subsequent fibrosis.

The term "substantially free" when referring to a compound or composition described herein means that there is less than 20% (by weight) of the designated compound or by-product (e.g., a saturated alcohol starting material) present, more preferably, there is less than 10% (by weight) of the designated compound or by-product, more preferably, there is less than 9% (by weight) of the designated compound or by-product, more preferably, there is less than 8% (by weight) of the designated compound or by-product, more preferably, there is less than 7% (by weight) of the designated compound or by-product, more preferably, there is less than 6% (by weight) of the designated compound or by-product, more preferably, there is less than 5% (by weight) of the designated compound or by-product, more preferably, there is less than 4% (by weight) of the designated compound or by-product, more preferably, there is less than 3% (by weight) of the designated compound or by-product, more preferably, there is less than 2% (by weight) of the designated compound or by-product, and most preferably, there is less than 1% (by weight) of the designated compound or by-product.

The term "substituents" refers to a group "attached" to a alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, e.g., C1, C2, C3, C4, C5, C6, C7, C8, C9, C10, C11, C12 straight or branched chain alkyl, cycloalkyl, haloalkyl, e.g., perfluoroalkyl such as $CF_3$, aryl, heteroaryl, aralkyl, heteroaralkyl, heterocyclyl, alkenyl, alkynyl, cycloalkenyl, heterocycloalkenyl, alkoxy, haloalkoxy, e.g., perfluoroalkoxy such as $OCF_3$, halo, hydroxy, carboxy, carboxylate, cyano, nitro, amino, alkyl amino, $SO_3H$, sulfate, phosphate, methylenedioxy e.g., —O—$CH_2$—O—, ethylenedioxy, oxo, thioxo, e.g., C=S, imino, e.g., alkyl, aryl, aralkyl, $S(O)_n$alkyl, $S(O)_n$ aryl, $S(O)_n$ heteroaryl, $S(O)_n$ heterocyclyl, i.e., wherein n is an integer between 0 and 2, amine, e.g., mono-, di-, alkyl, cycloalkyl, aralkyl, heteroaralkyl, aryl, heteroaryl, and combinations thereof, ester, e.g., alkyl, aralkyl, heteroaralkyl, aryl, heteroaryl, amide, e.g., mono-, di-, alkyl, aralkyl, heteroaralkyl, aryl, heteroaryl, and combinations thereof, sulfonamide, e.g., mono-, di-, alkyl, aralkyl, heteroaralkyl, and combinations thereof. In one aspect, the substituents on a group are independently any one single, or any subset of the aforementioned substituents. In another aspect, a substituent may itself be substituted with any one of the above substituents.

DETAILED DESCRIPTION

Compounds

In general, the compounds utilized in the composition of the present application are represented by formula (I):

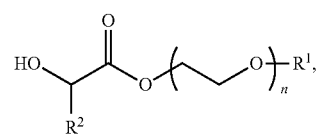

(I)

wherein n, $R^1$ and $R^2$ are as represented herein.

In one aspect, the invention features a composition containing an enantiomeric excess (ee) of the compound of Formula (I). For example, the composition can contain an ee of at least 50%, 75%, 90%, 95%, or 99%.

A compound described herein can also be in the form of a prodrug. Prodrugs of the compounds described herein are those compounds that readily undergo chemical changes under physiological conditions to provide the compounds of the present invention. In another exemplary embodiment, the prodrug is suitable for treatment/prevention of those diseases and conditions that require the drug molecule to cross the blood brain bather. In a preferred embodiment, the prodrug enters the brain, where it is converted into the active form of the drug molecule. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

A compound of the present invention can exist in an unsolvated form as well as a solvated form, including hydrated forms. In general, the solvated forms are equivalent to unsolvated forms and are encompassed within the scope of the present invention. Certain compounds of the present invention may exist in multiple crystalline or amorphous forms termed polymorphic forms. In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria included, for example, a material that is both a salt and a solvate is encompassed.

A compound described herein can be in the form of a metabolite. A metabolite may be a compound that is related to a compound described herein, as a form of such compound obtained in a human or animal body by action of the body on the administered form of the compound. For example, a metabolite may be a de-methylated analogue of a compound bearing a methyl group, which is obtained in the body after administration of the methylated compound as a result of action by the body on the methylated compound. A metabolite may also be a carboxylic-acid containing compound, which is obtained in the body after administration of the corresponding ester as a result of action by the body on the ester-containing compound.

Compositions of the Invention

The present invention features pharmaceutical compositions including any of the compounds described herein, either alone or in combination with one or more excipients. In some embodiments, the pharmaceutical composition is a composition that can be administered topically. In some embodiments, the pharmaceutical composition is a composition that can be administered to a subject orally. In some embodiments, the composition is a composition that can be administered bucally, vaginally, mucosally, nasally (e.g., intranasally) or parenterally (such as subcutaneous, intramuscular or intravenous injection), e.g., a liquid composition such as a solution, intranasally or via patch. In some embodiments, the composition is a solid composition, for example, a lyophilisate, which can be further processed prior to administering the composition to a subject, for example, the solid composition can be further processed to form a liquid composition such as a solution.

The compositions described herein, e.g., a composition including a compound of formula (I), can be used as sclerosant composition. These compositions may also include one or more analgesics, anesthetics and/or anti-inflammatory compounds.

Exemplary analgesic compounds include, but are not limited to, codeine, hydrocodone, hydromorphone, levorphanol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone.

Exemplary anesthetic compounds include, but are not limited to, benzocaine, butamben, dibucaine, lidocaine, oxybuprocaine, pramoxine, proparacaine, proxymetacaine, and tetracaine.

Exemplary anti-inflammatory compounds include, but are not limited to, aspirin, naproxen, ibuprofen, etodolac, cortisone (corticosteroids), antacids, sucralfate, proton-pump inhibitors, misoprostol, methotrexate, sulfasalazine, D-penicillamine, azathioprine, cyclophosphamide, chlorambucil, cyclosporine, leflunomide, etanercept, infliximab, anakinra, adalimumab, an NSAID and/or hydroxychloroquine.

In some embodiments, the compositions described herein consist essentially of a compound of formula (I). Certain compositions may also include one or more external analgesics and/or one or more moisturizers.

The compositions described herein, e.g., a composition including a compound of formula (I), may be used for treating or preventing varicose veins. The compositions are useful for topically treating topical varicose veins (e.g., in the form of a topical cream or ointment). Certain compositions described herein adhere well to the skin and thus are very effective topically. Certain methods involve topical application, particularly to skin.

Exemplary compositions may include one or more additional excipients. Said excipients may be selected from, but not limited to moisturizers, skin protectants, enhancer components, surfactants, and thickeners.

Moisturizers

Compositions of the present invention may include a moisturizer to increase the level of hydration of the skin. The moisturizer can be a hydrophilic material including humectants or it can be a hydrophobic material including emollients. A humectant is a polar hygroscopic material that increases hydration by drawing water from the environment to help retain water in the skin's upper layers. An emollient is a hydrophobic material that provides softness, lubricity and smoothness to the skin and often forms a thin occlusive film that increases hydration by reducing transepidermal water loss (TEWL). Exemplary hydrophilic moisturizers include, but are not limited to, water, polyhydric alcohols, lower alkyl ethers, N-methylpyrrolidone, lower alkyl esters, urea, amino acids, ethoxylated amides, sodium pyrrolidone carboxylic acid, and the lower monohydroxy alcohols and hydroxy acids discussed below as enhancers, as well as combinations thereof. Thus, a lower monohydroxy alcohol can function as both a hydrophilic compound and an enhancer. Preferably, the hydrophilic components include polyhydric alcohols, lower alkyl ethers, and short chain esters. More preferably, the hydrophilic components include polyhydric alcohols.

Exemplary hydrophobic moisturizers include, but are not limited to, short chain (i.e., C1-C6) alkyl or (C6-C12) aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12) diacids or (C4-C12) diols optionally substituted in available positions by —OH; (C2-C18) alkyl or (C6-C12) aryl esters of glycerol, pentaerythritol, ethylene glycol, propylene glycol, as well as polyethoxylated derivatives of these; (C12-C22) alkyl esters or (C12-C22) ethers of polypropylene glycol; (C12-C22) alkyl esters or (C12-C22) ethers of polypropylene glycol/polyethylene glycol copolymer; and polyether polysiloxane copolymers. Additional examples of hydrophobic components include cyclic dimethicones, including volatile cyclic silicones such as D4 and D5, polydialkylsiloxanes, polyaryl/alkylsiloxanes, silicone copolyols, cocoa butter, beeswax, jojoba oil, lanolin and derivatives, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22) alkyl and (C12-C22) alkenyl alcohols, and petroleum derived alkanes such as isoparafins, petrolatum, petrolatum USP, as well as refined natural oils (especially NF or USP grades) such as olive oil NF, cotton seed oil, castor oil, peanut oil, corn oil, seasame oil, safflower oil, soybean oil, sunflower oil and the like, and blends thereof. In certain preferred embodiments, the hydrophobic components useful in the compositions of the present invention include those selected from the group consisting of petrolatum USP and short chain (i.e., C1-C6) alkyl or (C6-C12) aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12) diacids or (C4-C12) diols optionally substituted in available positions by —OH (such as diisopropyladipate, diisopropylsebacate); (C1-C9) alkyl or (C6-C12) aryl esters of glycerol, pentaerythritol, ethylene glycol, propylene glycol (such as glyceryl tricaprylate/caprate); and mixtures thereof.

Skin Protectants

Compositions of the present invention may also include a skin protectant. Certain materials including some humectants or emollients are also useful at providing safe and effective skin protection. When used in the appropriate amount they temporarily protect injured or exposed skin from harmful stimuli and may help provide relief to such surfaces. Similarly, sunscreens may be included, which protect the skin from harmful ultraviolet radiation. Information concerning safe and effective skin protectants is provided in the Proposed Final Rulemaking for Fever Blister and Cold Sore Treatment Drug Products in the Skin Protectant Drug Products for Over-the-counter Human Use Monograph, published by the United States Food and Drug Administration in the Federal Register, Volume 51, Number 21, Jan. 31, 1990, pages 3362 to 3370.

Enhancer Component

Compositions of the present invention may optionally include an enhancer to protect against microbial activity (e.g., against gram negative bacteria). The enhancer component may include but is not limited to an alpha-hydroxy acid, a beta-hydroxy acid, other carboxylic acids, a (C1-C4) alkyl carboxylic acid, a (C6-C12) aryl carboxylic acid, a (C6-C12) aralkyl carboxylic acid, a (C6-C12) alkaryl carboxylic acid, a phenolic compound (such as certain antioxidants and parabens), a (C1-C10) monohydroxy alcohol, a chelating agent, or a glycol ether (i.e., ether glycol) and/or mixtures thereof.

Surfactants

Compositions of the present invention optionally may include one or more surfactants to emulsify the composition and to help wet the surface and/or to aid in contacting the microorganisms. In general, a "surfactant" refers to an amphiphile (i.e., a molecule possessing both polar and nonpolar regions which are covalently bound) capable of reducing the surface tension of water and/or interfacial tension between water and an immiscible liquid. Surfactants that may be employed in the present compositions include, but are not limited to include soaps, detergents, emulsifiers, surface active agents, and the like. The surfactant can be cationic, anionic, nonionic, or amphoteric. In preferred embodiments, the surfactant includes poloxamer, ethoxylated stearates, sorbitan oleates, high molecular weight crosslinked copolymers of acrylic acid and a hydrophobic comonomer, and cetyl and stearyl alcohols as cosurfactants.

Thickeners

Compositions of the present invention may also include thickeners that are soluble, swellable, or insoluble organic polymeric thickeners such as natural and synthetic polymers including polyacrylic acids, poly(N-vinyl pyrrolidones), cellulosic derivatives, silicone elastomers and xanthan or guar gums or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres such as those available under the tradenames "ZEOSPHERES" or "Z-LIGHT" from 3M Company, St. Paul, Minn. and/or combinations thereof.

Forms

The pharmaceutical compositions of this invention may be administered orally. Compositions suitable for oral administration may be in the form of capsules, cachets, pills, tablets, lozenges (using a flavored base, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

In addition, the compositions described herein may be administered topically, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

Generally, the compositions of this invention may also be in one of the following forms:

A hydrophobic or hydrophilic ointment wherein the composition is formulated with a hydrophobic base (e.g., petroleum, thickened or gelled water-insoluble oils, etc.) and optionally having a minor amount of a water soluble phase. Hydrophilic ointments generally contain one or more surfactants or wetting agents.

An oil-in-water emulsion wherein the compositions described may be formulated in which the antiviral component is emulsified into an emulsion comprising a discrete phase of a hydrophobic component and a continuous aqueous phase that includes water and optionally one or more polar hydrophilic material(s) as well as salts, surfactants, emulsifiers and other components. These emulsions may include water soluble or water-swellable polymers as well as one or more emulsifiers that help to stabilize the emulsion. These emulsions generally have higher conductivity values, as disclosed in U.S. Pat. No. 7,030,203.

A water-in-oil emulsion wherein the compositions described herein may be formulated so that the antiviral components are incorporated into an emulsion that includes a continuous phase of a hydrophobic component and an aqueous phase that includes water and optionally one or more polar hydrophilic material(s) as well as salts or other components. These emulsions may include oil-soluble or oil-swellable polymers as well as one or more emulsifier(s) that help to stabilize the emulsion.

Thickened aqueous gels refer to systems including an aqueous phase which has been thickened by suitable natural, modified natural or synthetic polymers as described herein. Alternatively, the thickened aqueous gels can be thickened using suitable polyethoxylated alkyl chain surfactants that effectively thicken the composition as well as other non-ionic, cationic or anionic emulsifier systems.

Hydrophilic gels refer to systems in which the continuous phase includes at least one water soluble or water dispersible hydrophilic component other than water. The formulations may optionally also contain water up to 20% by weight. Higher levels may be suitable in some compositions. Suitable hydrophilic components include one or more glycols such as polyols such as glycerin, propylene glycol, butylene glycols, polyethylene glycols (PEGS), random or block copolymers of ethylene oxide, propylene oxide, and/or butylene oxide, polyalkoxylated surfactants having one or more hydrophobic moieties per molecule, silicone copolyols, as well as combinations thereof. One of ordinary skill in the art will recognize and understand that the level of ethoxylation should be sufficient to render the hydrophilic component water soluble or water dispersible at 23° C. In most embodiments, the water content is less than 20%, preferably less than 10% and preferably less than 5% by weight of the composition.

Methods of Making Compounds as Described Herein

The compounds described herein and employed in the compositions described herein (e.g., a compound of formula I) can be made using a variety of synthetic techniques. One example of a preparation of the compounds described herein is illustrated below in Scheme 1.

Scheme 1.

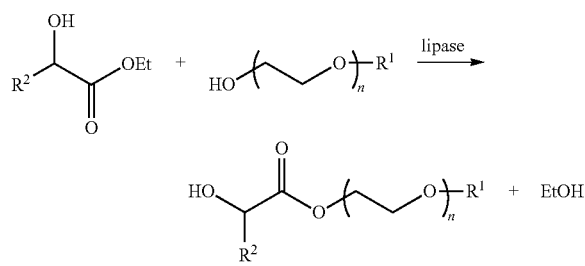

As can be appreciated by the skilled artisan, methods of synthesizing the compounds of the formulae herein will be evident to those of ordinary skill in the art. Additionally, any synthetic steps described herein may be performed in an alternate sequence or order to give the desired compounds. Synthetic chemistry transformations and protecting group methodologies, i.e., protection and deprotection, useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Reaction Mixtures

The present invention refers to compositions comprising a compound as described herein, including a reaction mixture, e.g., a reaction mixture that is present during a method or process described herein.

In certain embodiments, the methods described herein further comprise a solvent. In certain embodiments, the solvent is an organic solvent. In certain embodiments, the solvent is an aprotic solvent. Exemplary organic solvents include, but are not limited to, benzene, toluene, xylenes, acetonitrile, acetone, ethyl ether, tetrahydrofuran, methylene chloride, dichloroethane and chloroform, or a mixture thereof. In certain embodiments, the solvent is acetonitrile. In certain embodiments, the solvent is methylene chloride. In certain embodiments, the solvent is tetrahydrofuran. In certain embodiments, the solvent is dichloroethane. In certain embodiments, the solvent is benzene.

In certain embodiments, the reaction is a reaction below room temperature, e.g., a cooled reaction such as a reaction at a temperature of 0° C. or lower. In certain embodiments, the reaction is a heated reaction, e.g., a reaction occurring above room temperature. In certain embodiments, the reaction is a reaction run at room temperature. In certain embodiments, the reaction occurs under an inert atmosphere, e.g, an atmosphere of an inert gas such as nitrogen or argon. In certain embodiments, the reaction takes place under anhydrous conditions, e.g., conditions that are substantially free of water.

Described herein are compositions comprising a compound described herein, e.g., a compound of formula (I). In some embodiments, the compounds described herein are in a composition comprising a solvent, e.g., as a mixture such as a solution or a heterogeneous mixture. The composition can be free of compounds that would react with or degrade a compound described herein e.g., the composition can be substantially free of water and/or substantially free of any reactive gases.

EXAMPLES

Example 1. Preparation of Compounds

Polidocanol 41.32 g (70.9 mmol) Polidocanol, 21.07 g (178.4 mmol) ethyl lactate, 4.64 g Novozyme 435 and 1.00 g (11.9 mmol) sodium bicarbonate were added to a 100 mL 1-neck round bottom flask. The flask was then fitted to a rotary evaporator with the bath temperature set at 62° C. The pressure was slowly reduced to 15 mmHg under moderate rotation and the reaction mixture was held for 8 hours. Ethyl lactate (5.79 g, 49.0 mmol) was added to replenish the amount removed by distillation and the mixture was held an additional 16 hours at 62° C. and 15 mmHg. The round bottom flask was removed from the evaporator and the mixture was diluted with 20 mL petroleum ether. The solids were separated by vacuum filtration on a Buchner funnel with a #1 Whatman filter paper. The filtered solids were washed with 16 mL petroleum ether and the wash liquors were combined with the mother liquors. The combined filtrates were added to a 100 mL 1-neck round bottom flask and the flask was affixed to a rotary evaporator. The petroleum ether and excess ethyl lactate were distilled @ 15 mmHg with a bath temperature of 75-80° C. Upon completion of the distillation the pot was cooled and 38.19 g of Polidocanol lactate was obtained as a lightly colored waxy solid.

What is claimed is:

1. A composition configured for topical administration, comprising a compound of formula (I):

wherein
R$^1$ is a C$_{12}$ alkyl;
n is an integer from 4 to 10; and
R$^2$ is hydrogen, alkyl, aryl, heteroaryl, or heterocyclyl;
or a pharmaceutically acceptable salt thereof.

2. The composition of claim 1, wherein R$^2$ is alkyl.
3. The composition of claim 2, wherein R$^2$ is C$_{1-4}$ alkyl.
4. The composition of claim 1, wherein R$^2$ is aryl.
5. The composition of claim 1, wherein when R$^2$ is not hydrogen, the compound of formula (I) is a racemic mixture of a compound of formula (I).
6. The composition of claim 1, wherein when R$^2$ is not hydrogen, the compound of formula (I) is at least 90% enantiomeric excess of the R stereoisomer.
7. The composition of claim 1, wherein when R$^2$ is not hydrogen, the compound of formula (I) is at least 90% enantiomeric excess of the S stereoisomer.
8. The composition of claim 1, wherein the compound of formula (I) is represented by the following formula:

wherein n is 4.

9. The composition of claim 1, wherein the compound of formula (I) is represented by the following formula:

wherein n is 4.

10. The composition of claim 1, wherein the compound of formula (I) is represented by the following formula:

wherein n is 4.

11. The composition of claim 1, wherein the composition is a gel.

12. A composition configured for topical administration, comprising a compound of formula (I):

wherein
R$^1$ is a C$_{8-35}$ alkyl;
n is an integer from 4 to 10; and
R$^2$ is hydrogen, alkyl, aryl, heteroaryl, or heterocyclyl;
or a pharmaceutically acceptable salt thereof.

13. The composition of claim 12, wherein R$^1$ is a C$_{8-25}$ alkyl group.
14. The composition of claim 13, wherein R$^1$ is a C$_{10-20}$ alkyl group.
15. The composition of claim 14, wherein R$^1$ is a C$_{10-15}$ alkyl group.
16. The composition of claim 12, wherein R$^2$ is alkyl.
17. The composition of claim 16, wherein R$^2$ is C$_{1-4}$ alkyl.
18. The composition of claim 12, wherein R$^2$ is aryl.
19. The composition of claim 16, wherein R$^2$ is aralkyl.
20. The composition of claim 12, wherein when R$^2$ is not hydrogen, the compound of formula (I) is a racemic mixture of a compound of formula (I).
21. The composition of claim 12, wherein when R$^2$ is not hydrogen, the compound of formula (I) is at least 90% enantiomeric excess of the R stereoisomer.
22. The composition of claim 12, wherein when R$^2$ is not hydrogen, the compound of formula (I) is at least 90% enantiomeric excess of the S stereoisomer.
23. The composition of claim 12, wherein the composition is a gel.

* * * * *